United States Patent [19]

Weder

[11] Patent Number: 5,727,293
[45] Date of Patent: Mar. 17, 1998

[54] METHOD AND APPARATUS FOR CONTINUOUS CRIMPING OF THERMOPLASTIC THREADS

[75] Inventor: Eugen Weder, Fehrahorf, Switzerland

[73] Assignee: Maschinenfabrik Rieter AG, Winterthur, Switzerland

[21] Appl. No.: 718,575

[22] PCT Filed: Jan. 30, 1996

[86] PCT No.: PCT/CA96/00037

§ 371 Date: Oct. 2, 1996

§ 102(e) Date: Oct. 2, 1996

[87] PCT Pub. No.: WO96/23916

PCT Pub. Date: Aug. 8, 1996

[30] Foreign Application Priority Data

Nov. 29, 1994 [CH] Switzerland ............... 3394/95
Feb. 2, 1995 [CH] Switzerland ............... 284/95

[51] Int. Cl.$^6$ ................................................ D02G 1/00
[52] U.S. Cl. ............................. 28/249; 2/248; 2/250
[58] Field of Search ............... 28/217, 247, 248, 28/249, 250, 251, 254, 255, 256, 257, 263, 264

[56] References Cited

U.S. PATENT DOCUMENTS

| 4,404,718 | 9/1983 | Tajiri et al. |
|---|---|---|
| 4,608,736 | 9/1986 | Tajiri et al. |
| 4,866,822 | 9/1989 | Keedy, Jr. et al. ............... 28/250 |
| 4,908,919 | 3/1990 | Irvine ............................. 28/250 |
| 4,956,901 | 9/1990 | Koskol et al. .................. 28/255 |
| 5,088,168 | 2/1992 | Berger et al. .................. 28/248 |
| 5,351,374 | 10/1994 | Nabulon et al. ............... 28/248 |

FOREIGN PATENT DOCUMENTS

| 0428045 | 5/1991 | European Pat. Off. ......... 28/147 |
|---|---|---|
| 0554342 | 8/1993 | European Pat. Off. ......... 28/247 |
| 2933782 | 3/1981 | Germany ........................ 28/247 |
| 3609216 | 8/1987 | Germany ........................ 28/247 |
| 4435923 | 4/1995 | Germany ........................ 28/247 |
| 1 422 949 | 1/1976 | United Kingdom. |
| 9316218 | 8/1993 | WIPO .............................. 28/247 |

*Primary Examiner*—C. D. Crowder
*Assistant Examiner*—Larry D. Worrell, Jr.
*Attorney, Agent, or Firm*—Burns, Doane, Swecker & Mathis, L.L.P.

[57] ABSTRACT

The present invention relates to a method for continuous crimping of a thermoplastic material thread. According to the method, a transporting medium is pressurized, the transporting medium is heated, and a thread is transported, with the transporting medium, though a conveyor duct and out of an outlet opening of the conveyor duct at a transporting speed. The thread is transported from the outlet opening of the conveyor duct to an inlet opening of a stuffer box. The thread is compressed into a plug in the stuffer box by decelerating the thread. The plug is transported from an outlet opening of the stuffer box at a plug speed that is lower than the transporting speed such that the plug is cooled and opened to form a texturized and tensioned thread. At least one parameter of the plug is measured. The at least one measured parameter is compared with a target value of the at least one measured parameter. At least one signal is sent to at least one dependent control circuit when there is a difference between the at least one measured parameter and the target value of the at least one measured parameter. With the at least one dependent control circuit, at least one of a pressure of the transporting medium, a temperature of the transporting medium, and deceleration of the thread in response to the at least one signal is controlled. With at least one independent control circuit, at least one of a pressure of the transporting medium, a temperature of the transporting medium, and deceleration of the thread that are not controlled by the dependent control circuit is controlled. An apparatus for crimping thermoplastic threads is also disclosed.

34 Claims, 12 Drawing Sheets

Fig.5a
Fig.5b
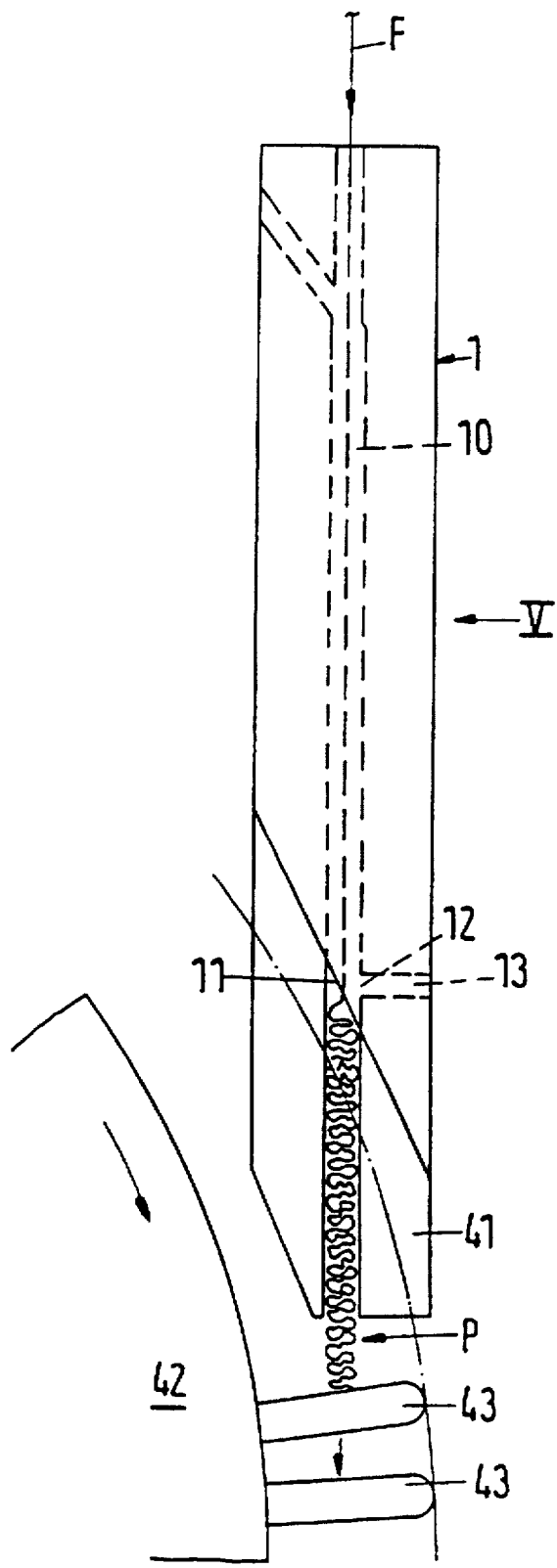
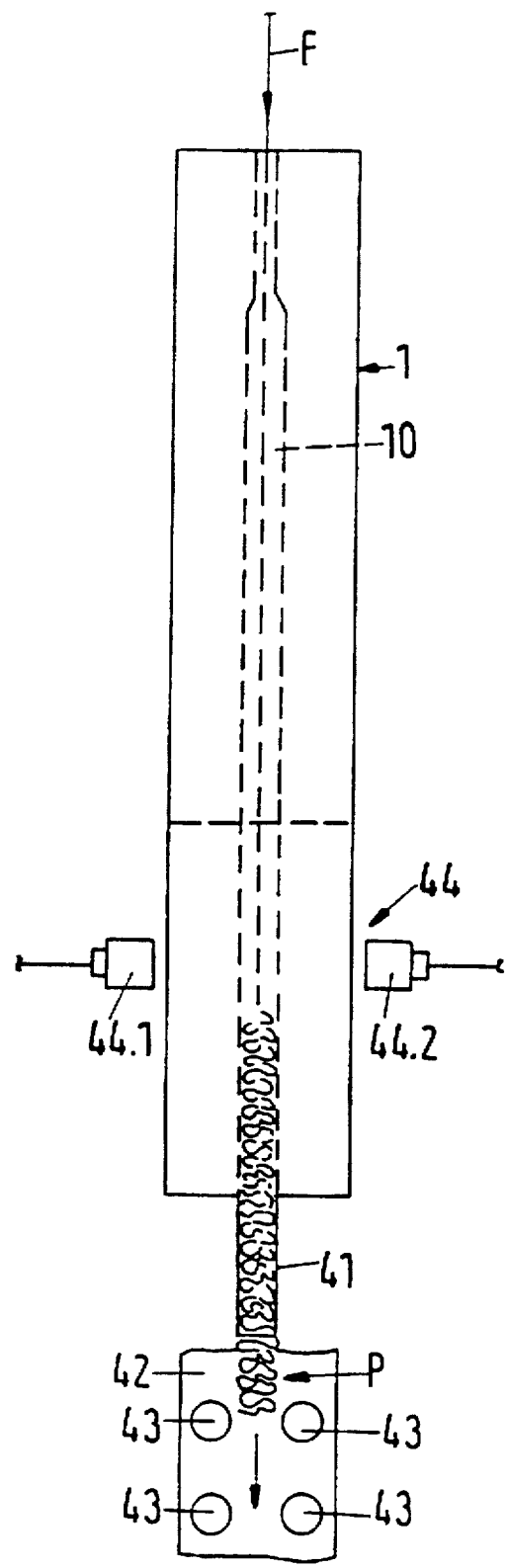

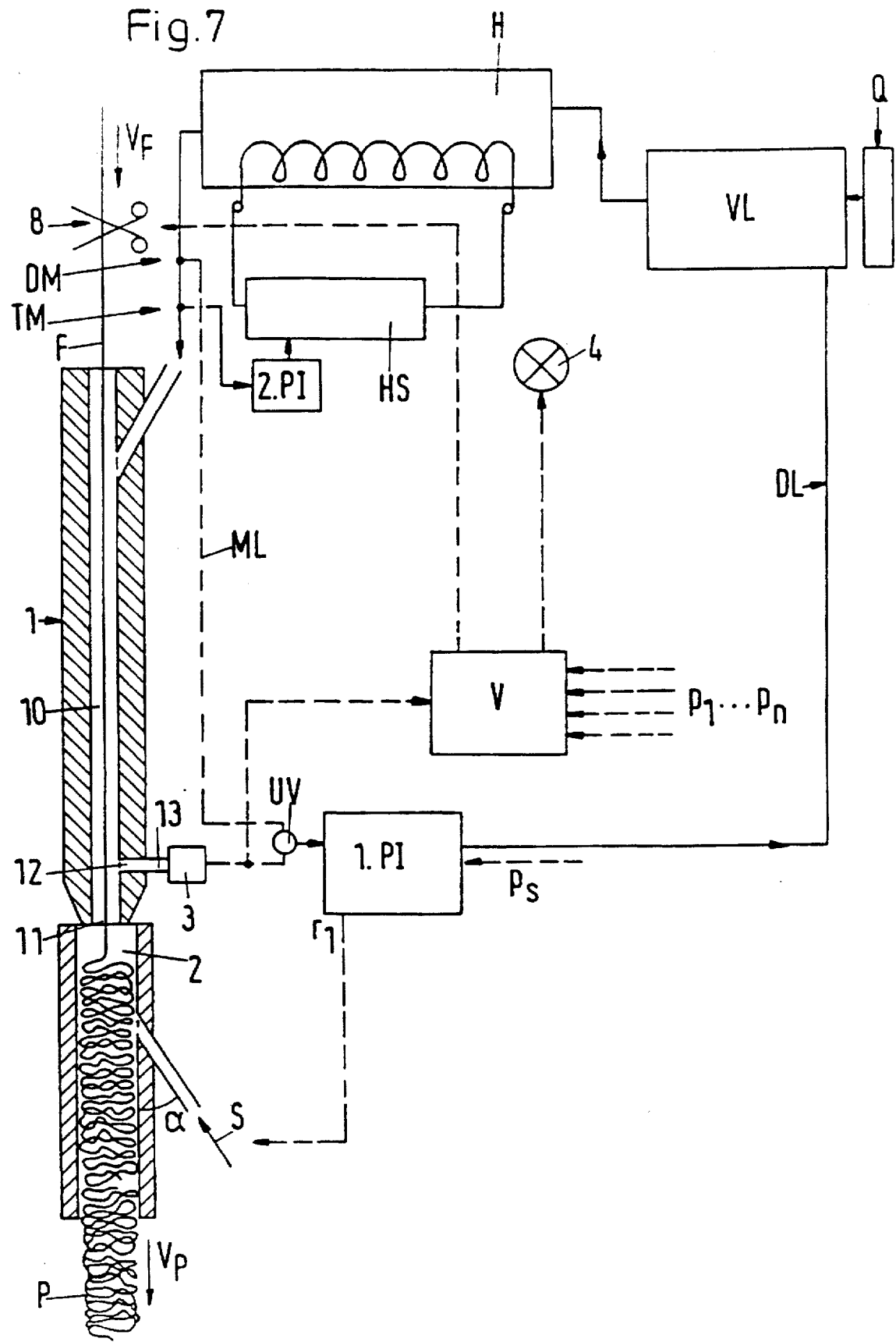

METHOD AND APPARATUS FOR CONTINUOUS CRIMPING OF THERMOPLASTIC THREADS

FIELD OF THE INVENTION

The present invention relates to the field of textile technology and concerns a method and an apparatus for continuous crimping of threads made from a thermoplastic material.

BACKGROUND AND SUMMARY OF THE INVENTION

For continuous crimping of threads (bundles of fibrils) of thermoplastic material these threads are conveyed through a duct e.g. by means of a hot transporting medium flowing under pressure in which process the threads are heated and then are transferred into a stuffer box designed in such a manner that the pressure of the transporting medium is released as the transporting medium escapes from the nozzle outlet opening. In the stuffer box the thread hits against a plug formed by thread that already had left the opening, in which process it is crimped. The plug is transported further at a speed lower than the thread speed in the conveyer duct, subsequently is cooled down and opened up to yield the texturized yarn.

The stuffer box in which the plug is formed can be limited by stationary perforated walls, formed e.g. by slats, which longitudinally surround the plug along its length. The plug is pushed by the pressure of the transporting medium to overcome the friction forces on the stuffer box walls throughout the stuffer box which it leaves via a plug opening arranged opposite the outlet opening which can be provided with a pair of delivery rolls which expels the plug in a controlled manner.

The stuffer box also can be limited partially only by stationary walls, and partially by walls which move at plug movement speed. A method and an apparatus for continuous crimping of thermoplastic threads using a stuffer box provided with walls, part of which move with the plug, are described e.g. in the European Patent Nr. 310890 applied for by the same applicant. The apparatus described comprises a texturing nozzle with a conveyer duct, an outlet opening and two shaped extension members extending therefrom in the direction of thread transport. For transporting the plug formed between the shaped extension members a duct formed by lateral guide means and extending along the circumference of a rotating plug transporting roll is provided into which the shaped extension members extend. The lateral guide means of this duct constitute the elements of the stuffer box wall moving with the plug. The plug moves from the stuffer box between the lateral guide means along part of the circumference of the plug transporting roll and then is transferred to another transporting element where it is cooled down and subsequently is opened up into a texturized yarn.

The thread is transported by means of a transporting medium through the conveyer duct and through the outlet opening into the stuffer box. Immediately beyond the outlet opening the pressure of the transporting medium is released. The thread hits the plug forming and is crimped in the process. Formation of the plug upon insertion of the thread at the start of production is initiated under the influence of a braking or stemming force acting temporarily, e.g. of an air stream directed against the thread. During operation an equilibrium is maintained between the compressing pressure of the transporting medium pushing the plug and the friction forces on the walls braking the plug, continuous plug formation and a constant plug movement speed being established and maintained.

The quality of the texturized yarn is closely related to the uniformity of the crimping process i.e. to the uniformity of plug formation. In the absence of a plug the thread is not crimped at all. If plug formation sets in at a distance too far from the outlet opening the plug density is reduced in such a manner that crimp no longer is sufficiently intense nor sufficiently permanent. This signifies that for high thread quality the position, consistency, and speed of movement, of the plug are to be maintained as constant as possible.

In all apparatuses known thus far for continuous crimping of threads of thermoplastic material using a texturing nozzle and a stuffer box irregularities in the plug formation can occur, especially phases in which plug formation occurs too far away from the outlet opening or plug formation does not occur at all, so called blow-outs. Depending on the type of apparatus used such blow-outs are of temporary nature, i.e. plug formation is resumed spontaneously without any action being taken, or the blow-outs are stationary, i.e. the machine must be stopped before regular plug formation is obtained again.

If defective plug formation can be discovered by visual inspection only, defects frequently are not detected at all or are detected too late, in such a manner that packages of the texturized thread contain defective thread portions, caused by undetected temporary blow-outs, which are detected only in a product manufactured from the thread. Stationary blow-outs which go undetected for a while can cause production of large quantities of reject threads.

It has been the goal of the invention according to the Swiss Patent Application 2052/92 dated Jun. 30, 1992, to propose a method and an apparatus for continuous crimping of threads of thermoplastic material, using which impaired yarn quality and production of rejects, caused by instabilities in plug formation, especially caused by blow-outs, can be avoided. This goal is achieved by a method according to which for continuous crimping of a thread of thermoplastic material the thread is heated, and using a flowing transporting medium is conveyed at a thread speed through a conveyer duct and through an outlet opening into a stuffer box, is impacted and compressed under the action of braking forces in the stuffer box into a plug, in which plug form it is transported on, at a plug speed lower than the thread speed, to the cooling and opening zones, the plug formation being monitored by sensor means in the area of the outlet opening and the measuring signals scanned being processed as measuring values for a closed loop control circuit for maintaining the plug formation constant or for activating stop devices, alarm or warning devices, or at the same time for control processes and for activation of said devices.

The corresponding device comprises a texturing nozzle with a conveyer duct and with a inlet opening for a thread, with an inlet opening for a transporting medium and with an outlet opening for the thread and transporting medium, and with a stuffer box, characterized in that in the area of the outlet opening sensor means are provided for monitoring this area.

The invention cited is based on continuous and automatic monitoring of the plug formation being used for control or alarm purposes. Monitoring is effected by sensor scanning of the area of the outlet opening, e.g. by measuring the static pressure or by measuring a parameter correlated to the static pressure, in the conveyer duct near the outlet opening in close vicinity outside the outlet opening, or by optical monitoring of the stuffer box near the outlet opening, and by further processing the signals scanned by the sensor monitoring means for open or closed loop control purposes, and/or for alarm purposes.

The static pressure in the conveyer duct corresponds to the differential between the total pressure which remains substantially constant and the dynamic pressure which is proportional to the square of the flow speed. If the conveyer duct is empty (in the absence of a thread), in which condition the transporting medium can flow through the duct unhampered by any thread, the static pressure is lowest the flow speed being high. If a thread is conveyed through the duct by the medium, the stationary pressure is higher compared to the stationary pressure in the duct in the absence of a thread the medium being stemmed by the thread. If a plug builds up in the stuffer box downstream from the outlet opening, the medium is stemmed further and the static pressure increases accordingly. Static pressure is higher the closer to the outlet opening formation of a plug sets in. Measuring the static pressure in close vicinity of the outlet opening can furnish direct indications on the state of plug formation.

Similar conditions prevail concerning the static pressure in the stuffer box immediately outside the outlet opening.

In the same manner the plug formation can be monitored using optical sensors. For good quality crimping the plug formation must set in as close as possible to the outlet opening, not beyond an empirically determined distance therefrom. If the plug formation point recedes further away from the outlet opening a blow-out occurs. Using an optical sensor monitoring the stuffer box in the area of the maximum distance tolerable of the plug formation point from the outlet opening occurrence of a blow-out can be detected.

As the plug formation depends on the stemming action in the stuffer box and on plug movement, plug formation can be maintained constant by controlling these parameters. This means that monitoring the plug formation, especially monitoring of the pressure in the area of the outlet opening can be integrated as a measurement parameter into a control circuit with a proportional/integral control member the actor members of which act upon the stemming effect exerted by the stuffer box walls and/or the plug transport, in particular the speed of plug movement.

The above mentioned patent CH 2059/92 thus concentrates on the operating conditions within the nozzle.

The present invention is based on the findings that the operating conditions with in a texturing nozzle are more complex than assumed in CH 2059/92. They can be influenced by operating parameters outside the nozzle and can influence operating parameters outside the nozzle itself. Plug formation thus can be monitored at a location situated at a distance from the plug itself.

Also, further actor parameters influencing the results can be considered other than the ones proposed in EP-554642A1. In particular it is proposed now that the pressure and/or the temperature of the texturing medium (transporting air), also called "feed air" is used as an actor parameter.

BRIEF DESCRIPTION OF THE DRAWINGS

The method according to the present invention and embodiments as design examples of the inventive apparatus are to be described in the following with reference to the Figures, the system according to CH 2059/92 being chosen as a starting point. It is shown in.

DETAILED DESCRIPTION

Figure 1:
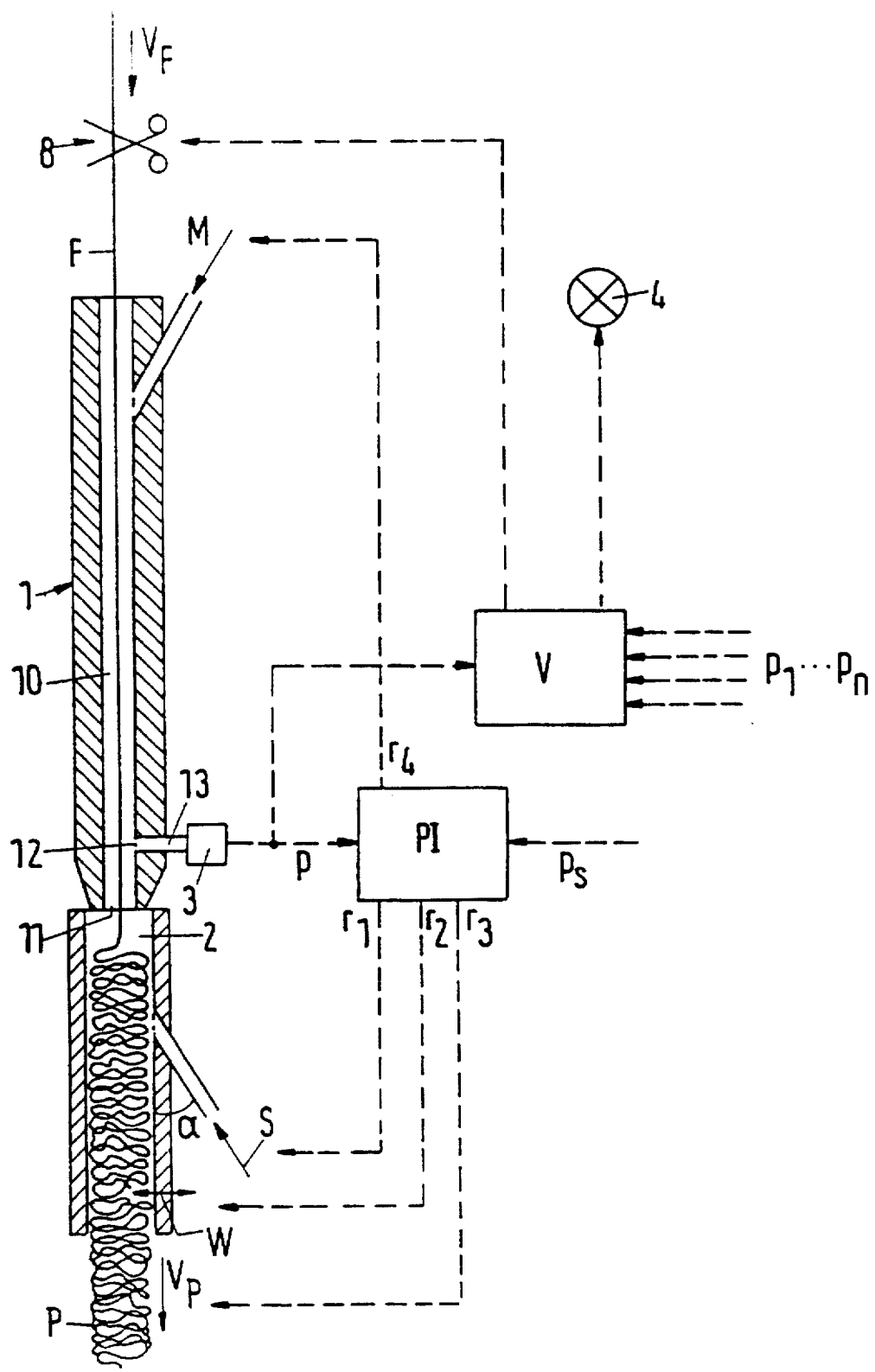
FIG. 1 a schematic lay-out of the apparatus according to EP-554642A1.

FIG. 1 shows a schematic lay-out of the apparatus according to EP-554642A1 based on which the method according to that application is to be explained. The apparatus comprises a nozzle element 1 with a conveyer duct 10 and an outlet opening 11 and adjacent downstream from it a stuffer box 2, which elements are shown in a section along the direction of movement of the thread F to be textured. The thread F is conveyed by means of a transporting medium M which is fed under pressure into the conveyer duct at the thread speed $V_F$ through the conveyer duct 10 and through the outlet opening 11. For heating the thread at the same time the transporting medium is provided at a raised temperature. The transporting medium M is fed under pressure into the conveyer duct 10 and its pressure is released outside the outlet opening 11. The thread F is transported through the conveyer duct and outside the outlet opening hits the plug P which is moved in turn at a plug movement speed $V_p$ and in subsequent steps is cooled down and is opened into a texturized thread.

Into the stuffer box 2 a stemming medium S can be fed under pressure against the thread under an angle μ with respect to the plug movement. The angle μ in this arrangement is to be chosen between 0° and 90° in such a manner that the flow direction of the stemming medium does not contain any component in the direction of the plug movement speed. The stemming medium S is used during the start-up period mainly but also during operation as required for initiating, or for ensuring, the plug formation by means of additional stemming action, the thread being stemmed by the stemming medium and being moved against the walls of the stuffer box and thus being additionally held back by the friction on these walls.

In the wall of the conveyer duct a measuring opening 12 is provided adjacent to which a hollow measuring room 13 is arranged. The measuring room 13 is closed except for the measuring opening and is provided with a pressure gauge 3, e.g. a piezo element, using which the pressure prevailing in the measuring room 13, which corresponds to the static pressure within the conveyer duct (area of the measuring opening), is measured.

The value p measured by the pressure gauge 3, which corresponds to the static pressure within the conveyer duct, is transmitted as measuring value into a proportional/integral P/I control device and/or into a comparator unit V. Applying the output signal ($r_1$, $r_2$, $r_3$ or $r_4$) of the control device PI either the aerodynamic stemming action in the stuffer box can be influenced by controlling the supply of the stemming medium $S(r_1)$, or the mechanical friction in the stuffer box can be influenced by control W of the stuffer box wall or of the geometry of the stuffer box ($r_2$), or of the plug movement speed by controlling the speed of a plug transporting means ($r_3$) arranged adjacent to the stuffer box, or by influencing the compression action by controlling the supply of the transporting medium $M(r_4)$ in such a manner that the compression pressure p corresponds to a pre-set target value $P_s$. The pre-set target value $P_s$ can be determined by experiments and can be transmitted to the control device, or can be determined by a calibrating measurement.

The actor devices (not shown in the Figure) of the control circuit are e.g. control valves for the supply of the stemming medium or of the transporting medium, a drive unit, using which a braking member is moved into the stuffer box or using which the stuffer box is narrowed in iris-fashion, or the drive unit of a possibly provided plug transporting means arranged adjacent to the stuffer box. Control of the supply of the stemming medium is best suited in apparatuses provided with stuffer boxes with partially moving walls, control of the stuffer box walls or of their geometry (e.g. the degree of taper of the stuffer box) is best suited for apparatuses provided with stationary stuffer box walls merely, in which arrangements the adaptations required are very small (in the range of tenths of a millimeter). An iris-type movement is best suited for stuffer boxes formed by individual stationary slats. Control of the plug movement speed can be effected only if the texturing device comprises a plug transporting means arranged adjacent to stuffer box, e.g. a needle studded roll.

According to the teachings of EP-554642A1 control of the supply of the transporting medium is less advantageous as it also influences the thread temperature and thus the crimping action, but as will be discussed in the following, it now is proposed that these parameters be influenced.

The measuring value generated in the pressure measurement also can be compared in a comparator unit V with at least one measuring limit value ($p_1 \ldots p_n$). If pre-set limit values are exceeded, e.g. an alarm lamp 4 can be activated, or the production can be stopped by severing (8) the thread. The function of the comparator unit is to be described in more detail in the following with reference to the FIGS. 2, 3 and 4.

The function of the control device PI can be effected by a proportional/integral control device commercially available on the market. For a combined control and comparator function an integral control device e.g. with an alarm band and with a stop band can be applied. If comparison merely but no control action is to be effected, the function of the comparator device V can be accomplished e.g. by a discriminator device with an adaptable threshold. The threshold values for this arrangement are determined experimentally. Of course the control function and/or the comparator function also can be established by means of software applications.

Figure 2:
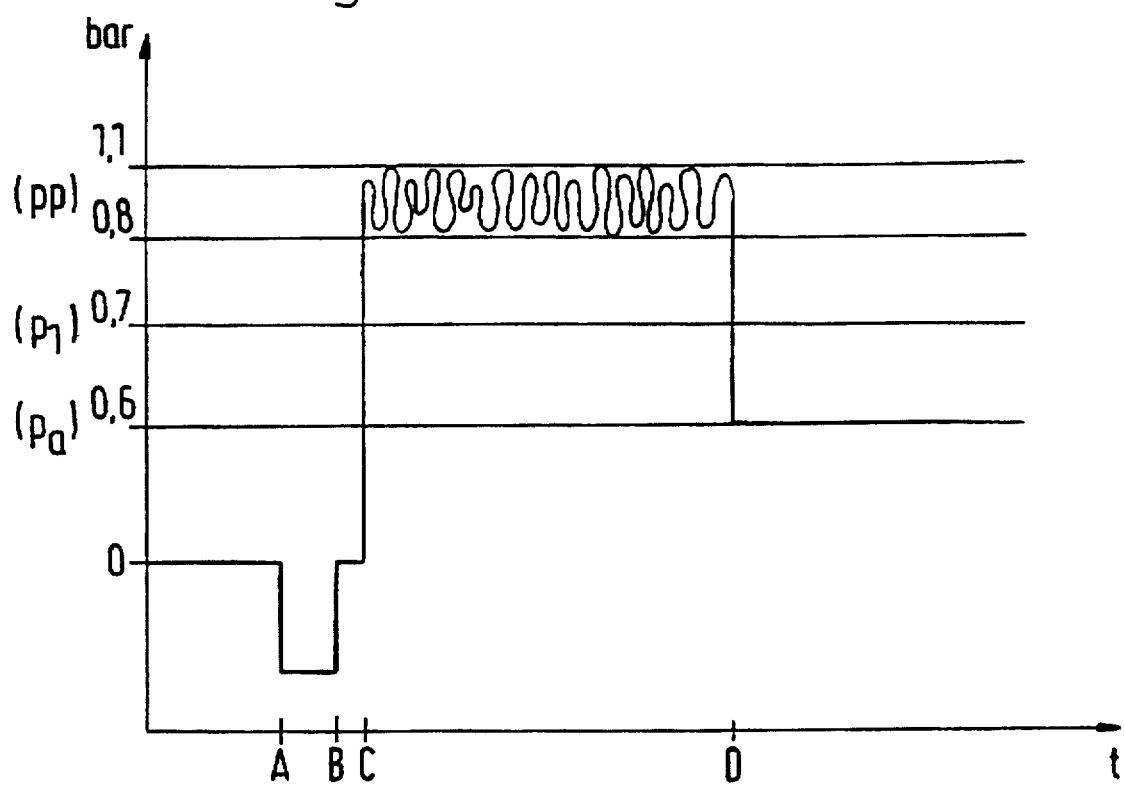
FIG. 2 a diagram of the measuring signal of a pressure measurement in the conveyer duct during the start-up phase of the apparatus according to FIG. 1 and during its operation, FIG. 3 a diagram of the measuring signal of a pressure measurement in the conveyer duct with control circuit, warning band and alarm band, FIG. 4 a diagram of the measuring signal of an optical sensor in the stuffer box during the start-up phase of the apparatus according to FIG. 1 and during its operation, FIGS. 5a and 5b a texturing nozzle with a stuffer box with a measuring opening for measuring the static pressure in the conveyer duct and means for optical monitoring of the stuffer box, FIG. 6 a texturing nozzle with a stuffer box with a means for monitoring the pressure in the stuffer box, FIG. 7 a schematic lay-out (similar to the one in FIG. 1) of a first embodiment of the present invention, FIG. 8 a further schematic lay-out of a second embodiment in which the device monitoring the operating parameter of the nozzle itself is complemented or is even replaced by a monitoring device scanning operating parameters outside the nozzle, and in FIGS. 9 and 11 a modification each of the embodiment according to FIG. 8, FIG. 10 a modification of the embodiment according to FIG. 7, FIG. 12 a schematic lay-out of a further embodiment, FIGS. 13 and 14 a modification each of the embodiment according to FIG. 12.
Figure 3:
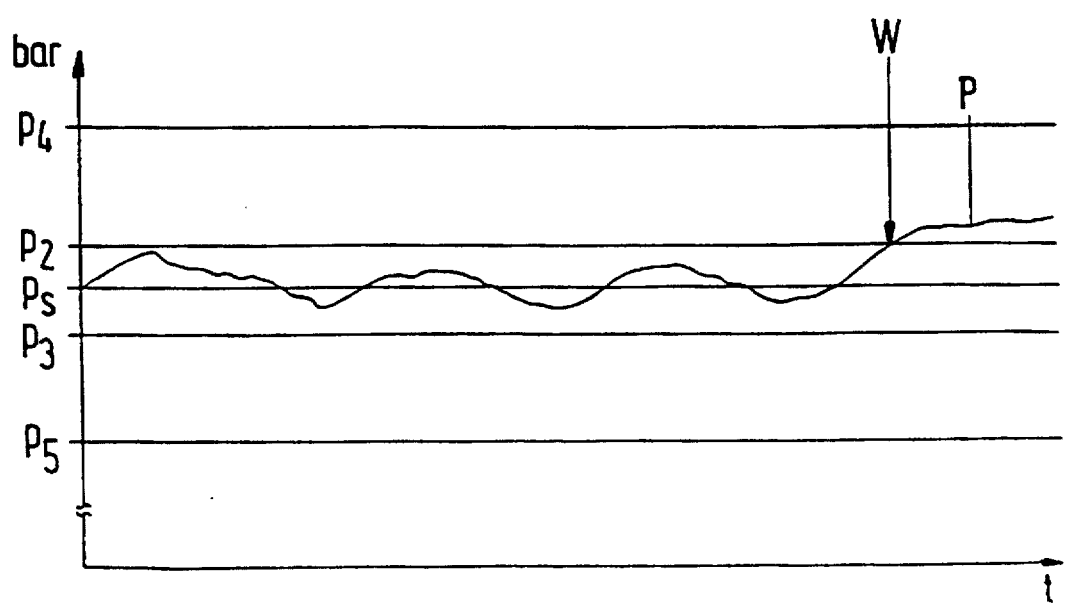
Figure 4:
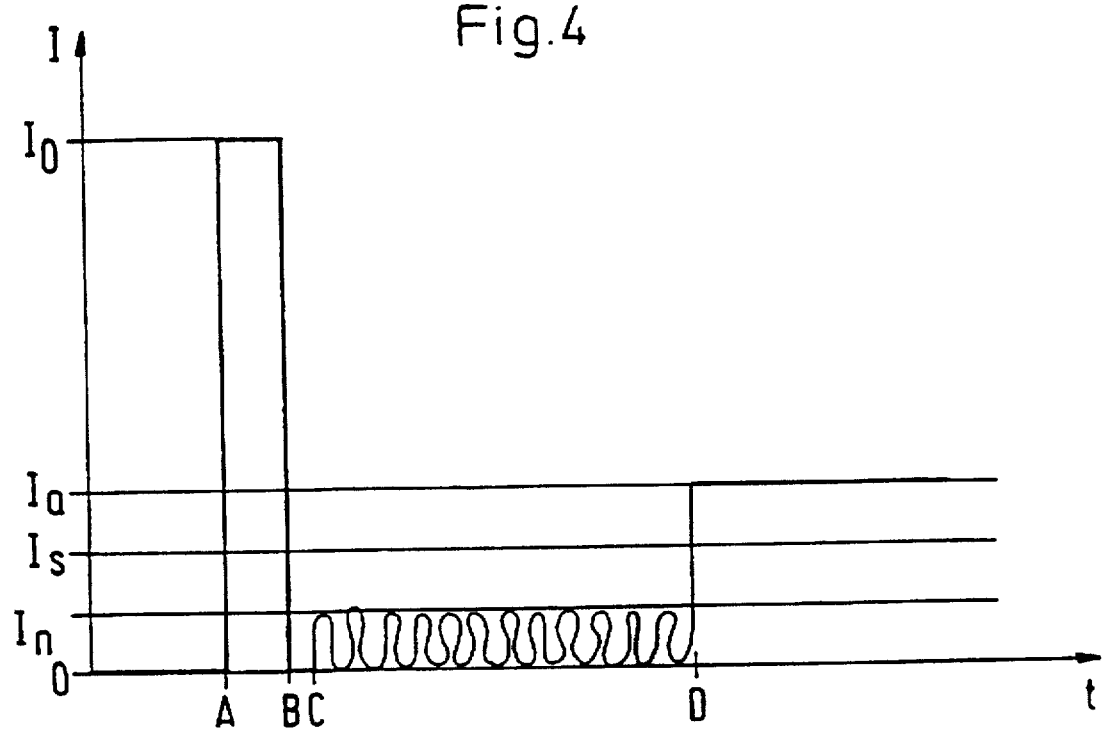

In the FIGS. 2, 3 and 4 examples of diagrams are shown of the measuring signal of a monitoring arrangement according to EP-554642A1. The measuring signal, or the physical value corresponding to the measuring signal, respectively, is plotted over time.

In the FIG. 2 a diagram is shown of the measuring signal in an arrangement using pressure measurement in the conveyer duct the measuring signal being analysed in a comparator device. The static pressure (measured in bar above or below atmospheric pressure) in the conveyer duct, corresponding to the measuring value p (e.g. electrical voltage), is plotted over the time axis t, the time span shown containing a start-up period of the apparatus, stationary operation, and the occurrence of a blow-out.

Up to the time moment A no transporting medium flows through the conveyer duct which can be closed or can be opened for preparatory steps, i.e. separated along the thread path in two duct sections. Up to this moment the static pressure in the nozzle is equal to the atmospheric pressure, the pressure measured thus equalling zero. At the time moment A the conveyer duct is closed and the transporting medium infeed is switched on, whereupon the transporting medium flows through the duct. The static pressure in the duct is lowered, and during the subsequent heating period remains constant. As soon as the texturing temperature is reached in the duct (at the time moment B) the infeed of the transporting medium is stopped, the duct is opened and the thread is inserted. At the time moment C the duct is closed and plug formation is initiated immediately, e.g. by activation of the thread stemming action applying the stemming medium S over a short time period. As the transporting medium is held back by the thread in the conveyer duct and at the plug in the stuffer box the static pressure in the conveyer duct increases and in a continuous and regular operation eventually settles in a pressure range corresponding to a range of measuring values pp. The operation can be called optimum if the range of measuring values pp is as small as possible and remains constant over long periods of time.

At the time moment D now a blow-out occurs, i.e. the point of plug formation recedes away from the outlet opening. Thus the stemming action exerted by the plug is reduced and the static pressure measured decreases, namely to a pressure corresponding to a measuring value $P_a$ which in the extreme case corresponds to the static pressure in the conveyer duct in complete absence of a stemming action of a plug.

By a measurement of the kind according to the one shown in the FIG. 2, in which the measuring value p is scanned and the plug formation is monitored, a threshold measuring value p is scanned and the plug formation is monitored, a threshold measuring value $p_1$ can be determined in such a manner that irregularities in the plug formation can be tolerated to a certain extent as long as they do not induce measuring value variations below the threshold measuring value $p_1$. The threshold measuring value $p_1$ is set at a value higher than the measuring value $P_a$ corresponding to a blow-out. The threshold measuring value $p_1$ is set low enough to maintain a sufficient margin with respect to the range of measuring values pp in such a manner that under regular operating conditions the measuring values p do not drop into its region. The threshold measuring value $p_1$ is set at a sufficiently high value that the irregularities of plug formation causing impaired thread quality and/or permanent blow-outs are detected as such.

In an apparatus according to the texturing device already mentioned initially in analogy to the European Patent Nr.

310890 e.g. the following pressure conditions were found: At an infeed pressure of the transporting medium of 7 to 7.5 bar the pressure range (range of measuring values pp) under regular plug formation conditions ranged from 0.8 to 1.1 bar (above atmospheric pressure), and the pressure during the occurrence of a blow-out (measuring value $p_a$) was measured as 0.6 bar, under which circumstances the threshold pressure (threshold measuring value $P_1$) had to be set at about 0.7 bar.

In the FIG. 3 an example is shown of a diagram of the signal in an arrangement in which pressure measurement is effected in the conveyer duct, with a control circuit, a warning band ($p_2 p_3$) and an alarm band ($p_4/p_5$).

Under optimum operating conditions the controlled measuring value should be maintained within the warning band. If the measuring value is outside the warning band but still within the alarm band, thread quality is not affected and production can be continued, but a warning signal W is generated (warning lamp, protocol printout) which indicates that maintenance operations (cleaning) are required soon. If the pressure measured exceeds the value $P_4$, the outlet opening is clogged, and if the pressure falls below $P_5$, a blow-out has occurred. In either case production must be stopped e.g. by cutting the thread.

In the FIG. 4 a diagram is shown of the measuring signal I transmitted by an optical sensor arranged in the stuffer box, plotted over the same time span as the diagram shown in the FIG. 2. The measuring signal I is e.g. the signal transmitted by an optical sensor consisting of a light source and a light sensitive cell arranged opposite each other within the stuffer box. The light emitted by the light source is directed towards the light sensitive cell, but is partially absorbed and dispersed by the thread and/or the plug. The measuring signal corresponds to the intensity of the light received by the light sensitive cell. This light intensity is high in the absence of thread in the stuffer box ($I_O$), and is lower ($I_a$) if a thread passes straight through the stuffer box, owing to the light absorption of the thread, which corresponds to a blow-out situation, and very low (range IHn) if a plug is present in the stuffer box. The threshold measuring value $I_s$ is set between $I_a$ and the upper limit of $I_n$.

In the FIGS. 5a and 5b two embodiments of the texturing apparatus according to EP-554642A1 are shown as examples, each provided with a nozzle element 1 with shaped extension members 41 functioning as a stuffer box. The texturing nozzle in the FIG. 5b is shown in rotated by 90° with respect to the arrangement shown in the FIG. 5a (seen in the direction of arrow V in the FIG. 5a). The thread as described before is conveyed through the conveyer duct 10 and through the outlet opening 11. Immediately outside the outlet opening plug formation sets in. The plug P formed is carried on by means of a plug transporting roll 42 between teeth 43.

In the apparatus according to the FIG. 5a the compressing pressure is measured in the conveyer duct. The apparatus comprises a measuring opening 12 which leads into a hollow measuring room 13. The hollow measuring room beyond the wall can be of any shape desired and adapted to the overall arrangement. The pressure gauge (not shown in the Figure) advantageously is arranged outside the walls of the conveyer duct.

In the apparatus according to the FIG. 5b plug formation is monitored optically. The apparatus comprises a light barrier arrangement 44 which can be provided as an alternative to the hollow measuring room and the pressure gauge. It comprises e.g. a light source 44.1 and a receiver 44.2 which are arranged opposite each other at the open sides of the stuffer box in such a manner that the receiver takes up the light emitted by the light source.

Figure 6:
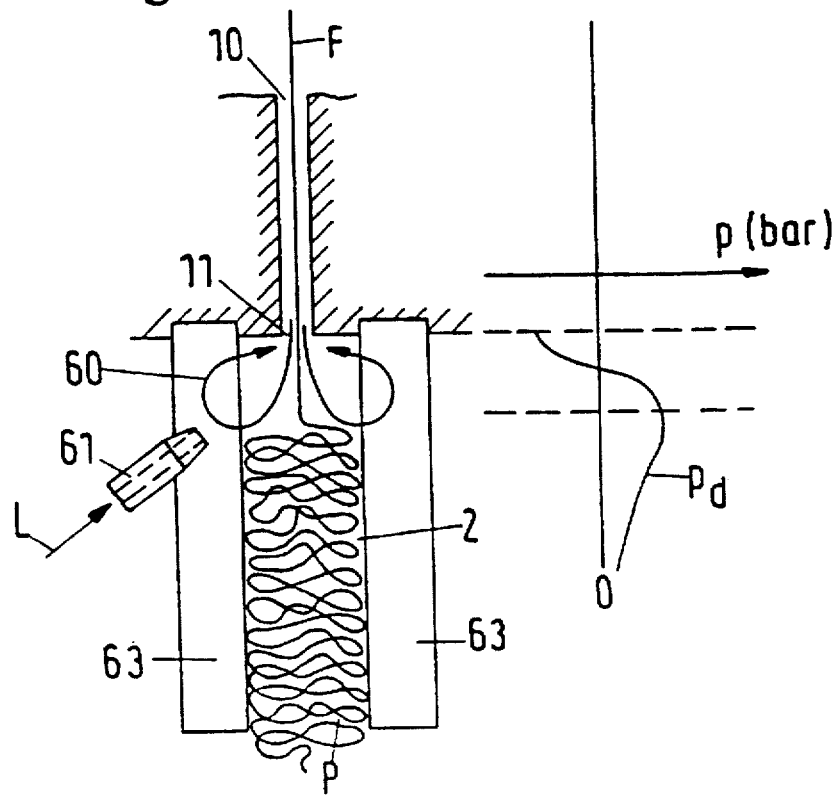

In FIG. 6 a further arrangement is shown schematically as an example of a monitoring arrangement for the pressure in the area of the outlet opening. In this arrangement the dynamic pressure is measured in a infeed duct for measuring air into the stuffer box immediately outside the outlet opening.

In the Figure again the conveyer duct 10 is shown through which a thread F is conveyed, and a stuffer box 2 in which a plug P is being formed. The stuffer box 2 in the arrangement shown as an example is limited by slats 63 arranged radially with respect to the plug. In the area of the outlet opening 11 the pressure of the transporting medium is released between the slats. Measurements indicate that between the plug P and the outlet opening 11 vortices (arrows 60) form in such a manner that in close vicinity of the outlet opening a flow from the stuffer box against the thread is generated near the plug. The shape of these vortices to a large extent depends on the geometrical lay-out of the outlet opening and of the stuffer box.

If during operation now between the outlet opening and the point of plug formation the pressure at the stuffer box wall is measured by means of a fluidic nozzle in function of the distance from the outlet opening, it is found that as indicated next to the schematic lay-out of the apparatus in the FIG. 6 a below atmospheric pressure (suction) is generated immediately outside the outlet opening which over a neutral zone increases up to a pressure maximum at the point of plug formation. If now e.g. at a distance from the outlet opening at which formation of the plug sets in under optimum production conditions a fluidic nozzle 61 of the type mentioned is installed, a statement concerning the position of the plug can be made based on the pressure measured in the nozzle. A measuring signal of this type can be analysed in analogy to the measuring signal of the sensor for the compression pressure in the conveyer duct.

A fluidic nozzle is understood to be a measuring nozzle through which measuring air is flowing at constant rate and in which the compressing pressure is measured. A fluidic nozzle of this type proves most advantageous as it is self-cleaning to a high degree owing to the measuring air stream.

The hollow measuring room, or the means monitoring the stuffer box, respectively, e.g. the light barrier arrangement, advantageously are arranged as close as possible to the outlet opening.

In the FIG. 7 first development according to the present invention is shown, the reference signs according to the FIG. 1 being re-used for designating identical elements. The additions according to the FIG. 7 comprise a source Q of compressed air, a controllable valve VL for influencing the pressure of the air from the source Q, a heater H for the air supplied from the valve VL and a control device HS for the heater H. The state of the air downstream of the heater H is controlled with respect to the pressure by means of the first PI-control device already mentioned with reference to the FIG. 1 and with respect to the temperature by means of a further, second PI-control device, and this air is supplied as feed air, i.e. as transporting medium or texturing medium respectively to the apparatus 1.

The first PI-control device is connected to the valve VL via the circuit DL and the second control device is connected to the control device HS via a circuit HL. Via the circuit DL the air pressure downstream of the valve VL can be used as actor force for maintaining the above mentioned compression pressure "P" as the controlled parameter within the pre-set tolerance limits.

A commercially available pressure gauge DM as well as a commercially available temperature measuring device TM can be provided between the heater H and the inlet opening for the feed air into the apparatus 1. The output signal from the device DM is transmitted via a circuit ML to a first PI-control device in such manner that this pressure can be maintained within pre-set limit values whereas the output from the device TM is transmitted via a circuit TL to a second PI-control device which in turn transmits its signal via a circuit HL to the control device HS.

In this arrangement either the compression pressure P or the pressure signal from the circuit ML is transmitted to the first P-control device, which can be effected using a commercially available switching valve UV. The compression pressure P, however, is permanently transmitted to the comparator unit V. The output signals from the first PI-control device are either the signal $r_1$ for control of the stemming medium S or the signal for the controllable valve VL. The stemming medium S, however, can be controlled also by an independent control arrangement (compare FIG. 13).

Figure 8:
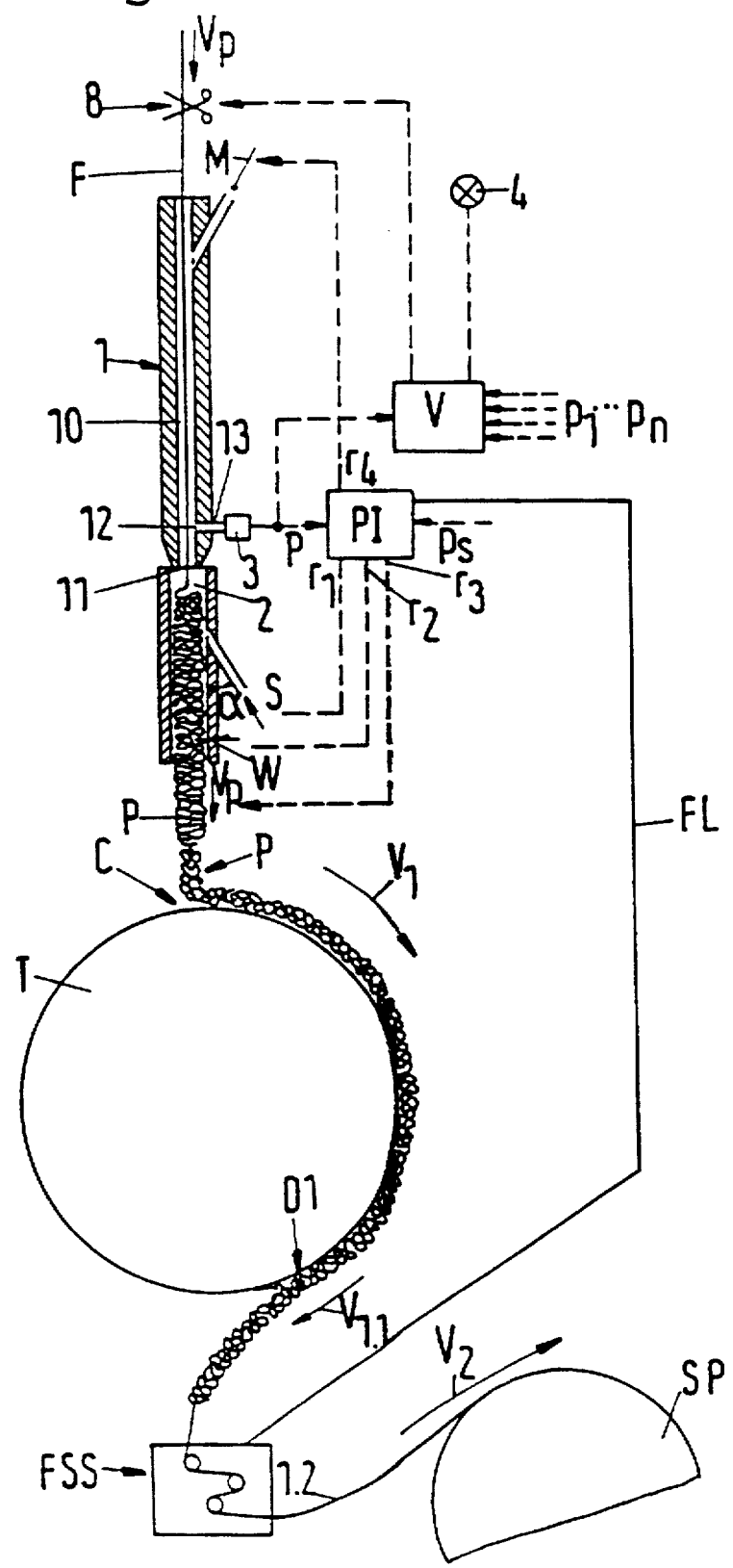

In the FIG. 8 a copy of the FIG. 1 is shown amended by the following new elements:

a rotatable cooling drum T which takes over the plug P.
a sensor FSS which measures the thread tensile force, also called thread tension, after take-off of the thread from the cooling drum.

The sensor FSS transmits its output signal via a circuit FL to the PI-control device and thus influences the operating parmeters which have been described with reference to the FIG. 1, in order to maintain the thread tensile force measured by the sensor FSS within pre-set limits.

The cooling drum T shown in the FIG. 8 is laid out according to EP-0 488 939. The plug P emerging from the stuffer box is transferred at the point C onto the cooling drum T which rotates at a constant surface speed $V_1$, and which is designed as a sieve drum or as a perforated roll. Air is sucked into the cooling drum which air holds the plug against the drum surface and at the same time cools it. The plug P moves with the surface of the drum and after reaching the Point D1 is lifted off the cooling drum by a corresponding deviating device (not shown) or by closing of the perforations of the cooling drum T in such a manner that the plug no longer is held by the below atmospheric pressure prevailing in the drum, i.e. that it is detached from the drum surface. The yarn 1.2 is taken off by the take-off package SP at a speed $V_2$.

Figure 9:
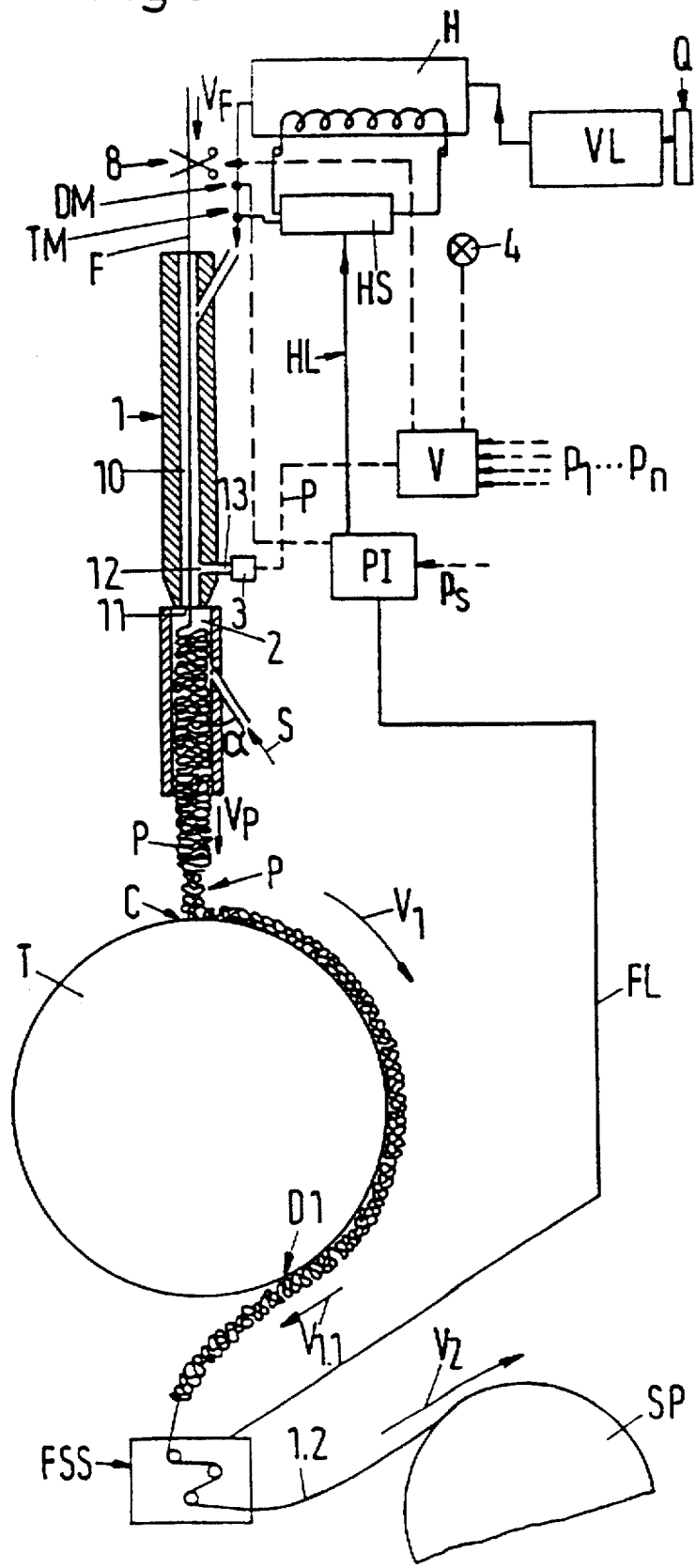

In the FIG. 9 the schematic lay-out according to the FIG. 7 is shown in part with amendments according to the amendments mentioned before with reference to the FIG. 8. The arrangement shown serves the same purpose as the arrangement according to the FIG. 8, the pressure, and/or the temperature respectively, of the transporting or texturing air being influenced in the present case in order to maintain the thread tension constant by transmitting the signal of the pressure gauge DM via the circuit ML to the PI-control device and by transmitting the signal of the temperature measuring device TM via the circuit TL to the control device HS.

Monitoring of the plug formation, however, opens up further possibilities also which are to be made accessible after further development of the principle proposed here. The plug formation is influenced by three types of operating parameters, namely:

1. parameters exerting an influence onto the thread which is supplied to the apparatus 1,
2. the operating parameters of the apparatus itself, and
3. the operating parameters of the subsequent processing devices, e.g. of the cooling drum.

If it proves possible to exclude, or to detect respectively, defects of one type, defects of other types can be detected owing to the monitoring of the plug formation. Application of defect detecting systems mentioned in the patent literature, e.g. mentioned in DE-A-44 14 517, can prove advantageous.

As already indicated in the discussion with reference to the FIGS. 8 and 9 the texturing device (the plug formation) also influences operating parameters which appear downstream from the device, e.g. the thread tension, and also the linear density of the thread. Based on the monitoring of such parameters the state of the texturing device can be assessed.

Known quality monitoring systems based on the measurement of thread tensile force can be found in the following patents:

DE-A-41 19 780
DE-A-44 13 549
U.S. Pat. No. 4,685,629
EP-C-207 471

Known quality monitoring systems based on the measurement of linear density of the yarn can be found in the following patents:

U.S. Pat. No. 3,731,069
U.S. Pat. No. 4,045,659
U.S. Pat. No. 3,885,232
U.S. Pat. No. 4,030,082
CH-C-551 923

It is to be noted additionally that the plug transporting means $r_3$ mentioned with reference to the FIG. 1 on page 8 or with reference to the FIG. 8 on page 15 either is the plug transporting roll 42 shown in the FIGS. 5a and 5b and mentioned on page 12 in connection with the method indicated and described in the European patent 310890, or is a plug transporting roll not shown here the surface of which is studded with pins taking up the plug and transferring it e.g. to a cooling drum T shown in the FIGS. 8 and 9 in which arrangement the speed Vp of the plug movement is influenced by means of the roll 42 mentioned or of a roll not shown the rotational speed of which is varied using the PI-control device.

Figure 10:
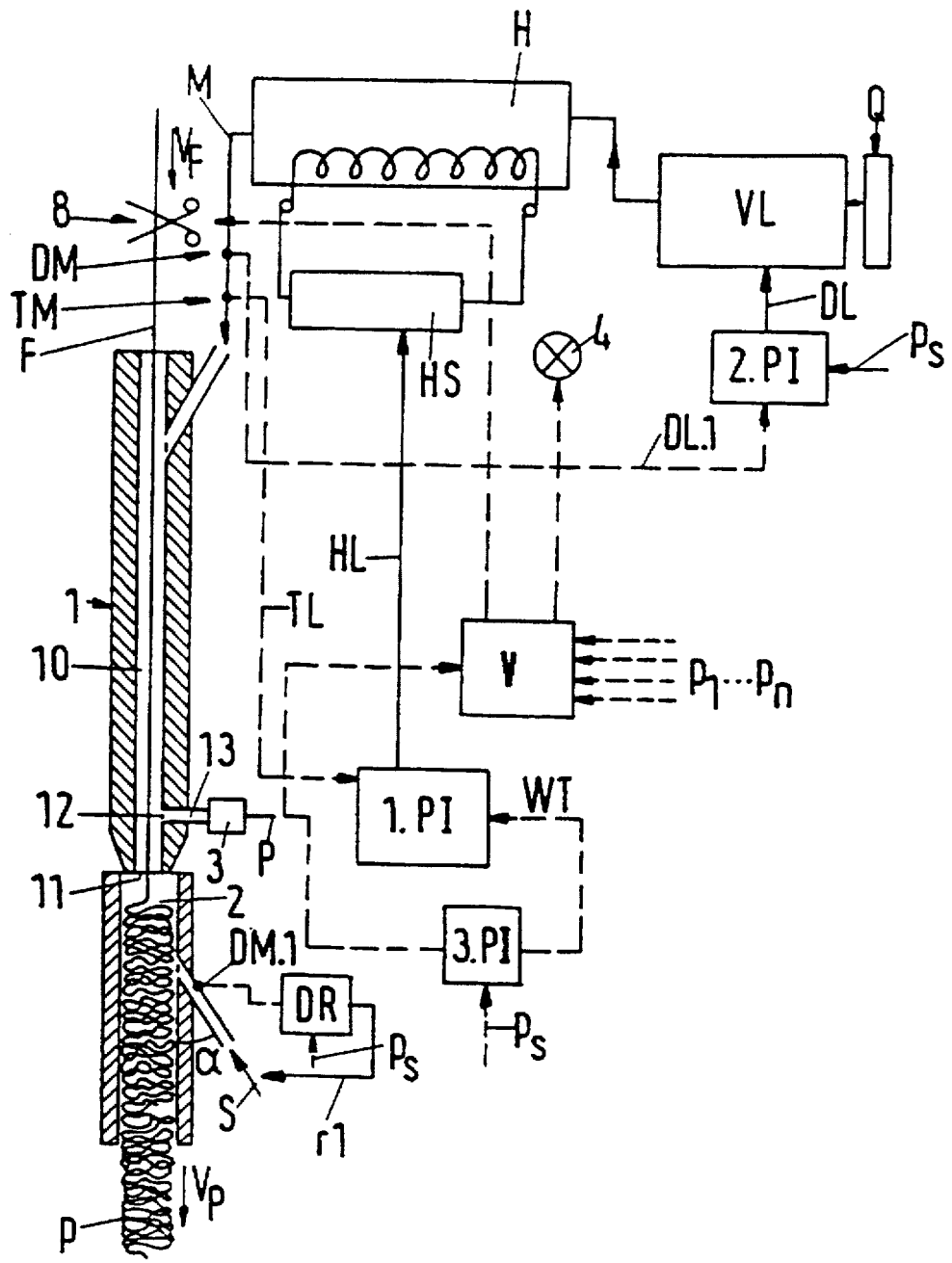

In the FIG. 10 the schematic lay-out according to the FIG. 7 is shown in part, the elements identical in the FIG. 10 and in the FIG. 7 being designated with the same reference signs and not being re-described.

In the FIG. 10 a first control circuit is shown controlling the heating of, and a second control circuit controlling the pressure of, the transporting medium M.

In the first control circuit the output signal of a first PI-control device, provided with a target value input WT, is transmitted to the control device HS via the circuit HL.

Furthermore the first PI-control device receives a temperature signal via a circuit TL from the temperature measuring device TM.

The target value WT of the first PI-control device is adapted by a third PI-control device provided with its own target value input PS, if the pressure signal p transmitted from the pressure gauge 3 deviates from the target value, i.e. that the plug in the stuffer box does not present the desired permeability, in which case the temperature of the thread is varied until the pressure p corresponds to the target value PS.

The second control circuit contains a second PI-control device, provided with a target value input PS, which controls the pressure in the controllable valve VL taking the signal from the pressure gauge DM into account which is transmitted to the second control device via the circuit DL.1. The output signals of the second PI-control device are transmitted to the controllable valve VL via the circuit DL.

For controlling the stemming medium S a separate control circuit is provided in which the signal of a pressure gauge DM.1 provided at the infeed tube for stemming the medium into the stuffer box is transmitted to a pressure control device DR provided with a target value input PS, in which arrangement the pressure control device DR controls the pressure of the stemming medium S.

Figure 11:
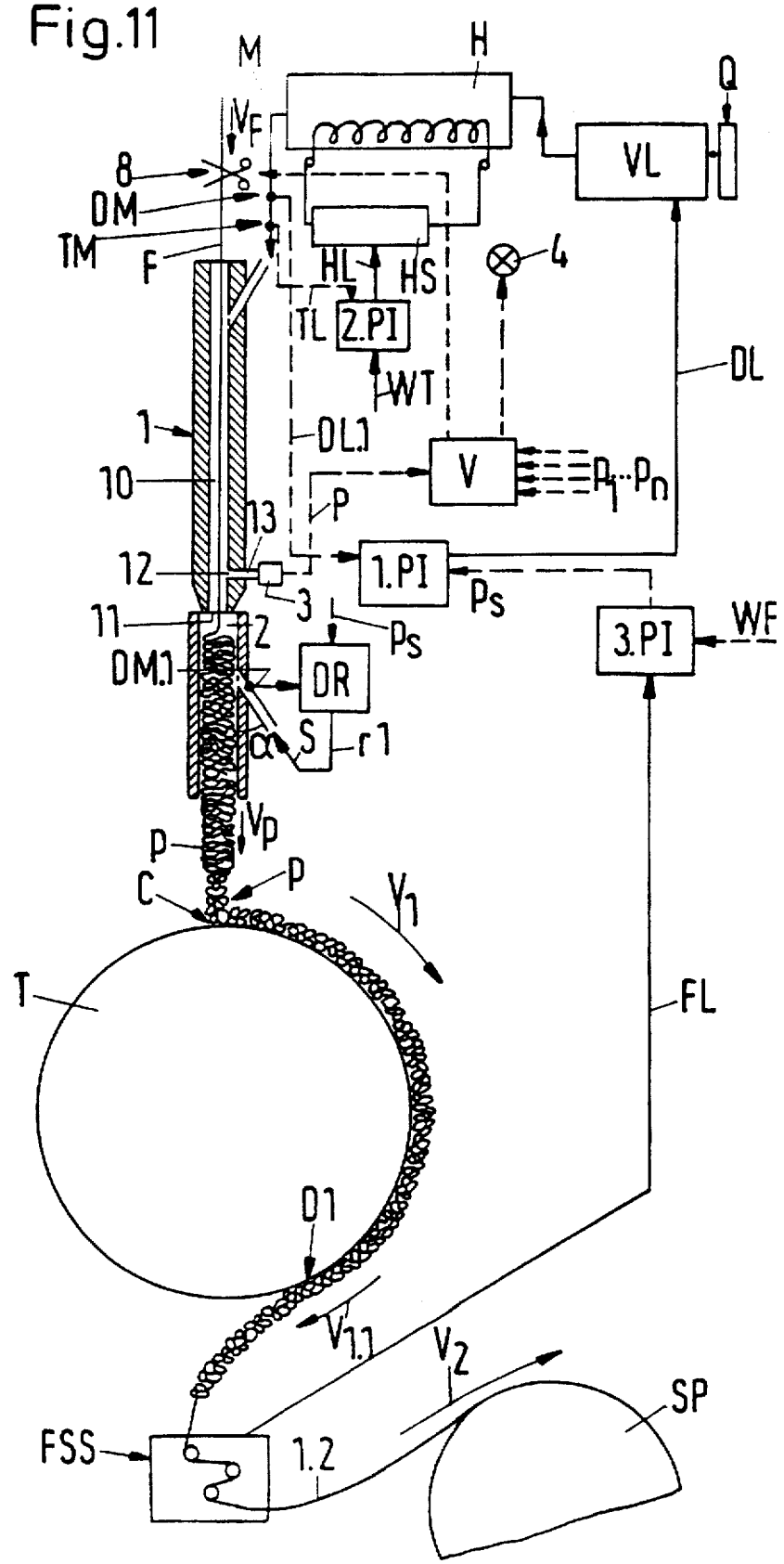

In the FIG. 11 the schematic lay-out according to the FIG. 9 is shown in part, the elements identical being designated using the same reference signs and their re-description being dispensed with here.

The arrangement shown in the FIG. 11 furthermore comprises a control circuit for controlling the pressure of the transporting medium in function of the thread tension measured using the thread tension measuring device FSS.

A second and a third control circuit, controls the temperature of the transporting medium, or the pressure of the stemming medium S, respectively, independently of the thread tension.

The first control circuit contains a first PI-control device provided with a target value input PS, which transmits an output signal via a circuit DL to the controllable valve VL and which receives an input signal from the pressure gauge DM via a circuit DL.1.

A signal from the thread tension measuring device FSS is transmitted via a circuit FL to a third PI-control device provided with a target value input WF in which arrangement the third PI-control device, if the thread tension signal differs from the target value WF, varies the target value PS of the first PI-control device until the thread tension signal corresponds to the pre-set target value WF.

The second control circuit comprises a second PI-control device provided with a target value input WT, which on one hand receives a temperature signal from the temperature measuring device TM via a circuit TL and on the other hand transmits a controlling signal via a circuit HL to the control device HS which controls the heater H.

A fourth control circuit controls the stemming air S in which arrangement the pressure gauge DM. 1 transmits a pressure signal to a pressure gauge DR provided with a target value input PS, an the pressure gauge DR generates the control signal $r_1$ using which the pressure of the stemming air S is controlled via a valve not shown here.

The second control circuit controls with a second PI-control device provided with a target value input WT, and controls the temperature of the transporting medium M.

In the FIGS. 12, 13 and 14 an alternative design example is shown concerning the assessment of the plug located on the cooling drum T, in which arrangement not the thread tension is measured for assessing the plug, but the position of the point on the cooling drum T at which the plug is opened again into a thread which subsequently is taken off by a take-off roll and is transferred to a winding device SP.

In this arrangement the location mentioned above on the cooling drum is detected by means of a light sensor LS which can be a light emitter and a light receiver or any means suitable for monitoring the location of this plug dissolving point and capable of transmitting a corresponding signal.

The signal given off by the sensor LS is transmitted via a circuit SL into a fourth PI-control device provided with a target value input WL, which varies a target value PS of a first PI-control device if the signal SL deviates from the target value WL until the signal SL coincides with the target value WL.

Figure 12:
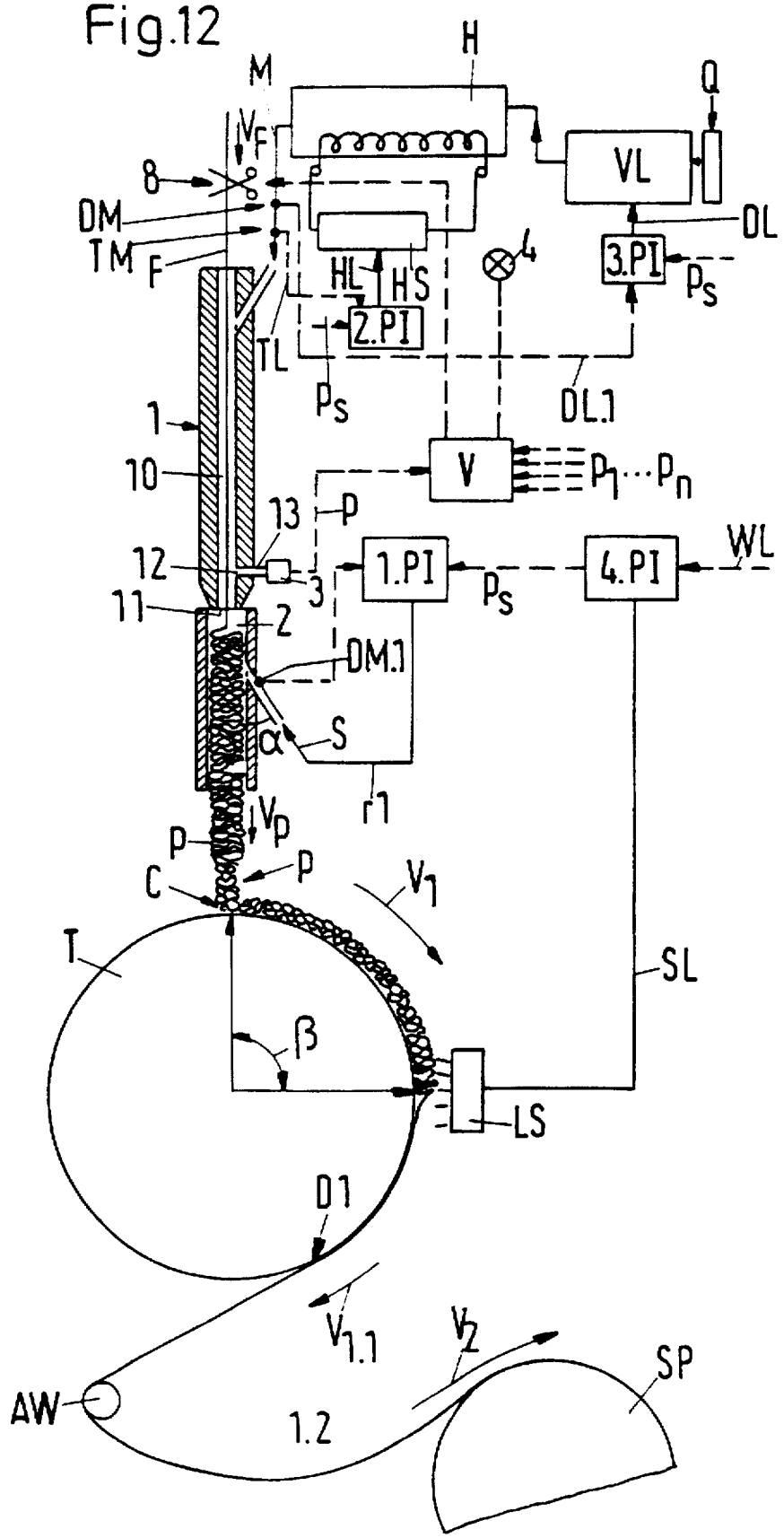

The first PI-control device of FIG. 12 in turn receives an input signal from a pressure gauge DM1 which measures the compressing pressure at the inlet tube of the stemming air and transmits the compressing pressure signal to the first PI-control device. The first PI-control device on the other hand generates the pressure signal $r_1$ using which the pressure of the stemming air S is controlled.

A second control circuit with a second PI-control device provided with a target value input WT, controls the temperature of the transporting medium M.

The second PI-control device receives a temperature signal from the temperature measuring device and transmits a controlling signal via a circuit HL to the control device HS.

A third control circuit controls the pressure of the transporting medium M in which arrangement a third PI-control device provided with a target value input PS receives a pressure signal from the pressure gauge DM via a circuit DL.1 and transmits a control signal via a circuit DL to the controllable valve VL.

Furthermore it is to be mentioned that the angle $\beta$ which is limited by the point C at which the plug is transferred to the cooling drum and by the point at which the plug is dissolved, is called cooling angle $\beta$.

Figure 13:
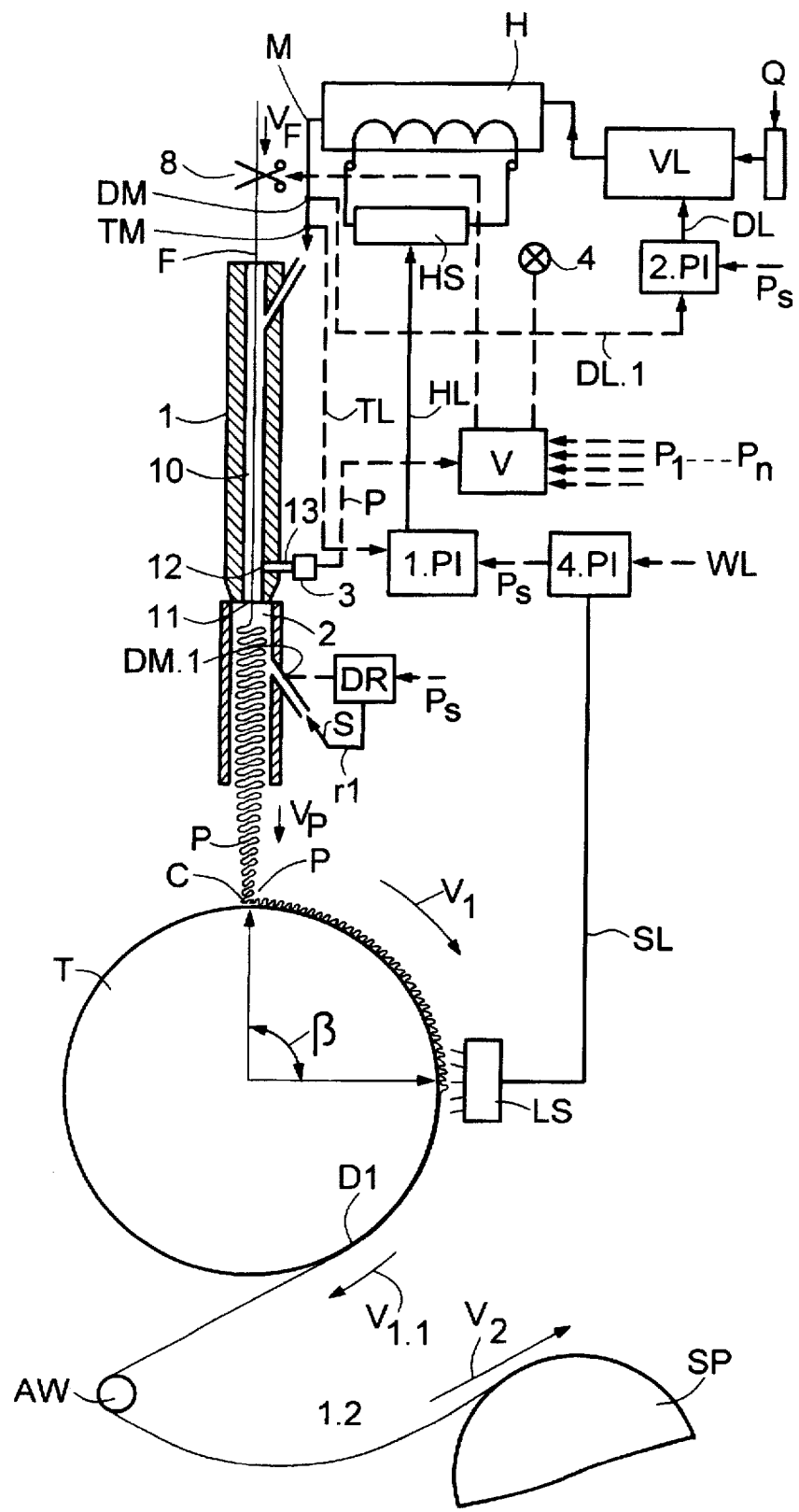

In the FIG. 13 the schematic lay-out of the FIG. 12 is shown in part, the identical elements being designated with the same reference signs and not being re-described again.

In the FIG. 13 three control circuits are shown, namely a first control circuit with a first PI-control device using which the temperature of the transporting medium is controlled in function of the position of the point on the cooling drum T at which the plug is opened or dissolved, and a second control circuit with a second PI-control device using which the pressure of the transporting medium M is controlled, as well as a third control circuit with a pressure control device DR using which the stemming air is controlled.

In connection with the first control circuit the signal SL of the light sensor LS in analogy to the arrangement shown in the FIG. 12 is transmitted to a fourth PI-control device provided with a target value input WL, in which arrangement the fourth PI-control device varies the target value input PS of the first PI-control device until the signal SL corresponds to the target value PL of the fourth PI-control device.

In this arrangement the first PI-control device receives a temperature signal from the temperature measuring device TM via the circuit TL and transmits a control signal via a circuit HL to the control device HS for controlling the heater which heats the transporting medium M.

The second control circuit corresponds to the third control circuit shown in the FIG. 12, the only difference being that the PI-control device is designated as the second PI-control device; therefore a further description of this control circuit is dispensed with.

The control circuit for the stemming air corresponds to the one shown in the FIG. 10, and in the FIG. 11 respectively.

Figure 14:
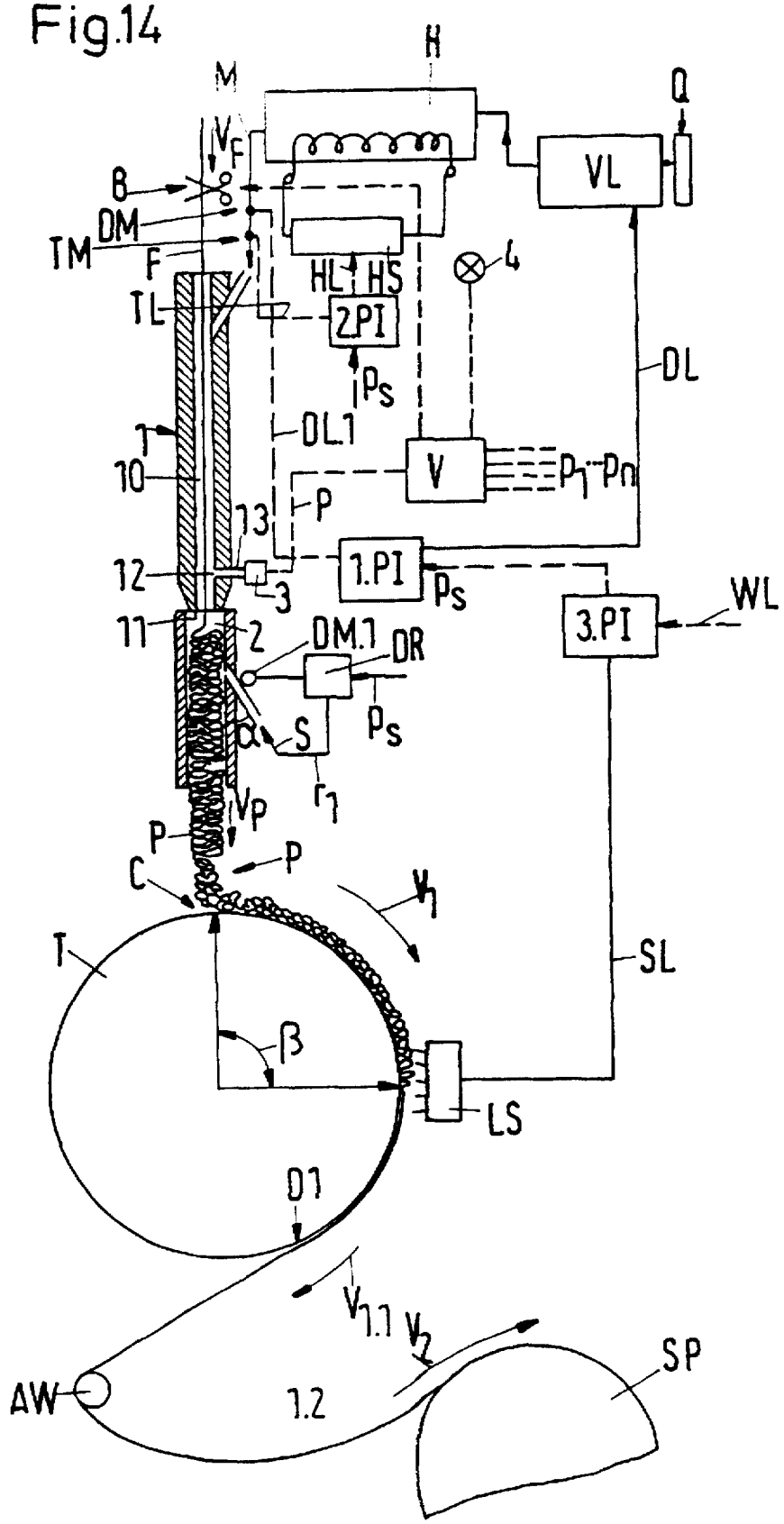

In the FIG. 14 part of the elements shown are identical to the ones shown in the FIGS. 11, 12 and 13; the elements identical thus are designated using the same reference signs and are not re-described here.

In the FIG. 14 also three control circuits are shown; similarly as in the FIG. 13, in which arrangement the first control circuit, however, does not control the temperature of the transporting medium M, but the pressure in function of the position of the point at which the plug on the cooling drum T is dissolved.

Accordingly the first PI-control device transmits a control signal via the circuit DL to the controllable valve VL and receives an input signal from the pressure gauge DM via the circuit DL.1.

The first PI-control device contains a target value input PS which is varied by a third PI-control device until the signal of the light sensor corresponds to a target value input WL of the third PI-control device.

The second control circuit comprises the second PI-control device provided with a target value input PS which receives a temperature signal from the temperature measuring device TM via the circuit TL and transmits a control signal via the circuit HL to the control device HS.

The control of the stemming air, which is effected in the third control circuit, is identical to the one described with reference to the FIGS. 10, 11 and 13.

It is to be noted that the present invention is not limited to the embodiments shown in the Figures but that within the scope of the invention a predetermined number of adjustment parameters and a predetermined number of measuring parameters can be combined, namely the adjustment parameter for adjusting the pressure of the transporting medium, the adjustment parameter for adjusting the temperature of the transporting medium for heating the thread, and the adjustment parameter for adjusting the stemming air flow for at least initiating the compression of the thread in the stuffer box, as well as the measuring parameter indicating the compression pressure in the conveyer duct, the thread tension as a further measuring parameter, as well as the cooling angle β, or the position respectively of the point at which the plug on the cooling drum is dissolved as a third measuring parameter, in which arrangement the adjusting parameters and the measuring parameters are combined in the framework of a matrix the adjusting parameters e.g. being listed in the abscissa direction and the measuring parameters being listed along the axis of ordinates, which matrix furnishes corresponding combinations. This signifies that within the scope of the present invention also other adjusting parameters and other measuring parameters can be chosen and can be combined.

I claim:

1. A method for continuous crimping of a thermoplastic material thread, comprising the steps of:

pressurizing a transporting medium;

heating the transporting medium;

transporting, with the transporting medium, a thread though a conveyor duct and out of an outlet opening of the conveyor duct at a transporting speed;

transporting the thread from the outlet opening of the conveyor duct to an inlet opening of a stuffer box;

compressing the thread into a plug in the stuffer box by decelerating the thread;

transporting the plug from an outlet opening of the stuffer box at a plug speed that is lower than the transporting speed such that the plug is cooled and opened to form a texturized and tensioned thread;

measuring at least one parameter of the plug;

comparing the at least one measured parameter with a target value of the at least one measured parameter;

sending at least one signal to at least one dependent control circuit when there is a difference between the at least one measured parameter and the target value of the at least one measured parameter;

controlling, with the at least one dependent control circuit, at least one of a pressure of the transporting medium, a temperature of the transporting medium, and deceleration of the thread in response to the at least one signal; and controlling, with at least one independent control circuit, at least one of a pressure of the transporting medium, a temperature of the transporting medium, and deceleration of the thread that are not controlled by the dependent control circuit.

2. The method according to claim 1, wherein thread tension in the texturized and tensioned thread and static pressure of the transporting medium in the conveyor duct are measured, and deceleration of the thread is controlled by the at least one dependent control circuit.

3. The method according to claim 2, wherein deceleration of the thread is led by the at least one dependent control circuit by controlling a stemming air flow blown into the stuffer box.

4. The method according to claim 2, wherein deceleration of the thread is controlled by the at least one dependent control circuit controlling a cross-section of the stuffer box.

5. The method according to claim 2, wherein deceleration of the thread is controlled by the at least one dependent control circuit controlling a speed of a plug transporting means for transporting the plug from the outlet opening of the stuffer box.

6. The method according to claim 5, wherein the plug is taken up by the plug transporting means transporting the plug on a needle-studded wheel.

7. The method according to claim 1, wherein thread tension in the texturized and tensioned thread is measured, and the temperature of the transporting medium is controlled by the at least one dependent control circuit.

8. The method according to claim 1, wherein the thread tension in the texturized and tensioned thread is measured, the pressure of the transporting medium is controlled by the at least one dependent control circuit, and deceleration of the thread is controlled by the at least one independent control circuit.

9. The method according to claim 8, wherein deceleration of the thread is controlled by the at least one independent control circuit controlling a stemming air flow blown into the stuffer box.

10. The method according to claim 1, wherein a static pressure of the transporting medium is measured, and the temperature of the transporting medium is controlled by the at least one dependent control circuit, and deceleration of the thread is controlled by the at least one independent control circuit.

11. The method according to claim 10, wherein deceleration of the thread is controlled by the at least one independent control circuit controlling a stemming air flow blown into the stuffer box.

12. The method according to claim 1, wherein a cooling angle of a cooling drum for cooling the plug is measured, the pressure of the transporting medium is controlled by the at least one dependent control circuit, and deceleration of the thread is controlled by the at least one independent control circuit.

13. The method according to claim 12, wherein deceleration of the thread is controlled by the at least one independent control circuit controlling a stemming air flow blown into the stuffer box.

14. The method according to claim 1, wherein a cooling angle of a cooling drum for cooling the plug is measured, the temperature of the transporting medium is controlled by the at least one dependent control circuit, and deceleration of the thread is controlled by the at least one independent control circuit.

15. The method according to claim 14, wherein deceleration of the thread is controlled by the at least one independent control circuit controlling a stemming air flow blown into the stuffer box.

16. The method according to claim 1, wherein a cooling angle of a cooling drum for cooling the plug is measured, and deceleration of the thread is controlled by the at least one dependent control circuit.

17. The method according to claim 16 wherein the pressure of the transporting fluid and the temperature of the transporting fluid are controlled by the at least one independent control circuit.

18. The method according to claim 16, wherein deceleration of the thread is controlled by the at least one independent control circuit controlling a stemming air flow blown into the stuffer box.

19. An apparatus for continuous crimping of a thermoplastic material thread, comprising:
- a conveyor duct having a passage for a thread and an outlet opening;
- a source of transporting medium in communication with the passage of the conveyor duct;
- a stuffer box having an inlet opening and an outlet opening, the thread being formed into a plug in the stuffer box;
- cooling means for cooling the plug;
- means for opening the plug so that the plug is in the form of a texturized and tensioned thread;
- means for measuring at least one parameter of the plug;
- at least one dependent control circuit for controlling at least one of a pressure of the transporting medium, a temperature of the transporting medium, and deceleration of the thread;
- at least one independent control circuit for controlling at least one of the pressure of the transporting medium, the temperature of the transporting medium, and deceleration of the thread that are not controlled by the dependent control circuit; and
- means for comparing the at least one measured parameter with a target value of the at least one measured parameter and sending at least one signal to the at least one dependent control circuit when there is a difference between the at least one measured parameter and the target value of the at least one measured parameter, the at least one dependent control circuit controlling the at least one of the pressure of the transporting medium, the temperature of the transporting medium, and deceleration of the thread in response to the at least one signal.

20. The apparatus as set forth in claim 19, wherein the measuring means includes means for measuring thread tension in the texturized and tensioned thread and means for measuring the pressure of the transporting medium, and the at least one dependent control circuit includes means for controlling deceleration of the thread.

21. The apparatus as set forth in claim 19, wherein the measuring means includes means for measuring thread tension in the texturized and tensioned thread and means for measuring the pressure of the transporting medium, and the at least one dependent control circuit includes means for controlling pressure of the transporting medium.

22. The apparatus as set forth in claim 19, wherein the measuring means includes means for measuring thread tension in the texturized and tensioned thread and means for measuring the pressure of the transporting medium, and the at least one dependent control circuit includes means for controlling temperature of the transporting medium.

23. The apparatus as set forth in claim 19, wherein the measuring means includes means for measuring thread tension in the texturized and tensioned thread, and the at least one dependent control circuit includes means for controlling temperature of the transporting medium.

24. The apparatus as set forth in claim 19, wherein the measuring means includes means for measuring the pressure of the transporting medium, and the at least one dependent control circuit includes means for controlling temperature of the transporting medium.

25. The apparatus as set forth in claim 24, wherein the at least one independent control circuit includes means for controlling deceleration of the thread.

26. The apparatus as set forth in claim 25, wherein the means for controlling deceleration of the thread includes means for blowing stemming air into the stuffer box.

27. The apparatus as set forth in claim 19, wherein the measuring means includes means for measuring thread tension in the texturized and tensioned thread, the at least one dependent control circuit includes means for controlling pressure of the transporting medium, and the at least one independent control circuit includes means for decelerating the thread.

28. The apparatus as set forth in claim 27, wherein the means for controlling deceleration of the thread includes means for blowing stemming air into the stuffer box.

29. The apparatus as set forth in claim 19, wherein the cooling means includes a cooling drum, and the opening means causes the plug to open after having traveled through a cooling angle on the cooling drum, the measuring means includes means for measuring a size of the cooling angle, the at least one dependent control circuit includes means for controlling deceleration of the thread, and the at least one independent control circuit includes means for controlling temperature of the transporting medium and means for controlling pressure of the transporting medium.

30. The apparatus as set forth in claim 29, wherein the means for controlling deceleration of the thread includes means for blowing stemming air into the stuffer box.

31. The apparatus as set forth in claim 19, wherein the cooling means includes a cooling drum, and the opening means causes the plug to open after having traveled through a cooling angle on the cooling drum, the measuring means includes means for measuring a size of the cooling angle, the at least one dependent control circuit includes means for controlling temperature of the transporting medium, and the at least one independent control circuit includes means for controlling pressure of the transporting medium.

32. The apparatus as set forth in claim 31, wherein the means for controlling deceleration of the thread includes means for blowing stemming air into the stuffer box.

33. The apparatus as set forth in claim 19, wherein the cooling means includes a cooling drum, and the opening means causes the plug to open after having traveled through a cooling angle on the cooling drum, the measuring means includes means for measuring a size of the cooling angle, the at least one dependent control circuit includes means for controlling pressure of the transporting medium, and the at least one independent control circuit includes means for controlling temperature of the transporting medium.

34. The apparatus as set forth in claim 33, wherein the means for controlling deceleration of the thread includes means for blowing stemming air into the stuffer box.

* * * * *